United States Patent
Kim et al.

(10) Patent No.: US 9,707,552 B1
(45) Date of Patent: Jul. 18, 2017

(54) CATALYST COMPOSITION COMPRISING PHOSPHORUS-BASED LIGAND AND HYDROFORMYLATION PROCESS USING THE SAME

(71) Applicant: LG CHEM, LTD., Seoul (KR)

(72) Inventors: Mi Young Kim, Daejeon (KR); Min Ji Choi, Daejeon (KR); Sung Shik Eom, Daejeon (KR); Dong Hyun Ko, Daejeon (KR); Da Won Jung, Daejeon (KR); Tae Yun Kim, Daejeon (KR)

(73) Assignee: LG CHEM. LTD., Seoul (KR)

( * ) Notice: Subject to any disclaimer, the term of this patent is extended or adjusted under 35 U.S.C. 154(b) by 0 days.

(21) Appl. No.: 15/107,361

(22) PCT Filed: Oct. 19, 2015

(86) PCT No.: PCT/KR2015/011011
§ 371 (c)(1),
(2) Date: Jun. 22, 2016

(87) PCT Pub. No.: WO2017/010618
PCT Pub. Date: Jan. 19, 2017

(30) Foreign Application Priority Data

Jul. 13, 2015 (KR) .................. 10-2015-0098902

(51) Int. Cl.
*C07C 45/50* (2006.01)
*B01J 31/00* (2006.01)
*B01J 31/24* (2006.01)

(52) U.S. Cl.
CPC .......... *B01J 31/2404* (2013.01); *C07C 45/505* (2013.01); *B01J 2231/321* (2013.01); *B01J 2531/822* (2013.01)

(58) Field of Classification Search
CPC .... C07C 45/50; C07C 45/505; B01J 31/2404; B01J 2231/321; B01J 2531/822
USPC .......................................... 568/454
See application file for complete search history.

(56) References Cited

U.S. PATENT DOCUMENTS 6,153,800 A   11/2000  Gelling et al.

FOREIGN PATENT DOCUMENTS

| EP | 2 445 920 B1 | 3/2014 |
|---|---|---|
| KR | 10-2010-0084519 A | 7/2010 |
| KR | 10-2010-0092169 A | 8/2010 |
| KR | 10-1095775 B1 | 12/2011 |
| WO | 2006098685 A1 | 9/2006 |

*Primary Examiner* — Sikarl Witherspoon
(74) *Attorney, Agent, or Firm* — Dentons US LLP

(57) ABSTRACT

Disclosed are a catalyst composition containing a phosphorous-based ligand and a hydroformylation process using the same. More specifically, disclosed are a catalyst composition containing a monodentate phosphite ligand, a monodentate phosphine ligand and a transition metal catalyst, wherein the total content of the entire ligand including the monodentate phosphite ligand and the monodentate phosphine ligand is 1 to 33 moles, based on 1 mole of the transition metal catalyst, and a hydroformylation method using the same.

The present invention has an effect of providing a catalyst composition which reduces an N/I (ratio of normal to iso) selectivity of aldehydes produced by hydroformylation of an olefin-based compound and exhibits superior catalytic activity and stability, and a hydroformylation method of an olefin-based compound using the catalyst composition.

13 Claims, No Drawings

CATALYST COMPOSITION COMPRISING PHOSPHORUS-BASED LIGAND AND HYDROFORMYLATION PROCESS USING THE SAME

TECHNICAL FIELD

This application is a National Stage Entry of International Application No. PCT/KR2015/011011, filed on Oct. 19, 2015, and claims the benefit of and priority to Korean Application No. 10-2015-0098902, filed on Jul. 13, 2015, all of which are hereby incorporated by reference in their entirety for all purposes as if fully set forth herein.

The present invention relates to a catalyst composition containing a phosphorous-based ligand and a hydroformylation process using the same. More specifically, the present invention relates to a catalyst composition which reduces an N/I ratio (ratio of normal to iso) of aldehyde produced by hydroformylation of an olefin-based compound and exhibits superior catalytic activity and stability, and a hydroformylation process of an olefin-based compound using the same.

BACKGROUND ART

A hydroformylation reaction, wherein linear (normal) and branched (iso) aldehydes, in which the number of carbon atoms is increased by one, are prepared by reacting various olefins with carbon monoxide (CO) and hydrogen ($H_2$), commonly called "synthetic gas", in the presence of a homogeneous organometallic catalyst and a ligand was first found by Otto Roelen in 1938 in Germany.

Generally, the hydroformylation reaction known as an oxo reaction is an industrially important reaction in the homogeneous catalyst reaction and various aldehydes including alcohol derivatives are produced and used all over the world through the oxo process.

Various aldehydes synthesized through the oxo reaction may undergo condensation reaction of aldol or the like and may then be converted into various acids and alcohols containing a long alkyl group through oxidization or hydrogenation. In particular, the hydrogenated alcohol obtained by this oxo reaction is referred to as an oxo alcohol. The oxo alcohol is widely industrially used for solvents, additives, materials for various plasticizers, synthetic lubricants and the like.

In this regard, conventionally, since the value of linear aldehyde derivatives (normal aldehydes) among aldehydes that are products of the oxo reaction is high, most of studies associated with catalysts have focused on increasing the ratio of linear aldehydes. However, recently, since products obtained by using branched-aldehydes (iso-aldehyde), for example, isobutyric acid, neopentyl glycol (NPG), 2,2,4-trimethyl-1,3-pentanediol, isovaleric acid and the like, as raw materials, instead of linear aldehydes, have been developed, a great deal research has been continued to increase selectivity of the iso-aldehydes. Accordingly, there is a need for developing catalysts which reduce an N/I (normal/iso) selectivity of aldehyde while exhibiting excellent catalytic stability and activity.

PRIOR ART DOCUMENT

Patent Document

Patent Document 1. KR 2001-0052204 A

DISCLOSURE

Technical Problem

Therefore, the present invention has been made in view of the above problems, and it is one object of the present invention to provide a catalyst composition which reduces an N/I (normal/iso) ratio (selectivity) of aldehyde produced by hydroformylation of an olefin-based compound and exhibits superior catalytic activity and stability.

It is another object of the present invention to provide a hydroformylation method of an olefin-based compound using the catalyst composition.

The objects and other objects of the present invention can be accomplished by the present invention described below.

Technical Solution

In accordance with the present invention, the above and other objects can be accomplished by the provision of a catalyst composition including a monodentate phosphite ligand represented by the following Formula 1, a monodentate phosphine ligand represented by the following Formula 2, and a transition metal catalyst represented by the following Formula 3, wherein the total content of the entire ligand including the monodentate phosphite ligand and the monodentate phosphine ligand is 1 to 33 moles, based on 1 mole of the transition metal catalyst,

[Formula 1]

[Formula 2]

wherein $R_1$, $R_2$, $R_3$, $R'_1$, $R'_2$ and $R'_3$ each independently represent: a substituted or unsubstituted alkyl group having 1 to 20 carbon atoms; a substituted or unsubstituted cycloalkyl or cycloalkenyl group having 5 to 20 carbon atoms group; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted heterocyclic group having 4 to 36 carbon atoms, wherein the heteroalkyl group, the heteroaryl group and the heterocyclic group contain one or more atoms selected from the group consisting of N, O and S, and when $R_1$, $R_2$, $R_3$, $R'_1$, $R'_2$ and $R'_3$ are substituted by a substituent, the substituent is nitro (—$NO_2$), fluorine (—F), chlorine (—Cl), bromine (—Br) or an alkyl group having 1 to 20 carbon atoms, $$M(L^1)_x(L^2)_y(L^3)_z \qquad \text{[Formula 3]}$$

wherein M is one selected from the group consisting of cobalt (Co), rhodium (Rh), iridium (Ir), ruthenium (Ru), iron (Fe), nickel (Ni), palladium (Pd), platinum (Pt) and osmium (Os), $L^1$, $L^2$ and $L^3$ each independently represent one selected from the group consisting of hydrogen, carbonyl (CO), cyclooctadiene, norbornene, chlorine, triphenylphosphine (TPP) and acetylacetonato (AcAc), and x, y and z each independently represent 0 to 5, with the proviso that all of x, y and z are not zero.

In accordance with another aspect of the present invention, there is provided a hydroformylation method of an olefin-based compound including reacting an olefin-based compound with a synthetic gas ($CO/H_2$) of carbon monoxide and hydrogen in the presence of the catalyst composition, to prepare aldehyde.

Effects of the Invention

The present invention has an effect of providing a catalyst composition which reduces an N/I (normal/iso) ratio of aldehydes produced by hydroformylation of an olefin-based compound and exhibits superior catalytic activity and stability.

In addition, the present invention has an effect of providing a hydroformylation method of an olefin-based compound using the catalyst composition.

BEST MODE

Hereinafter, the present invention will be described in detail.

The present inventors found that, when both a monodentate phosphite ligand and a monodentate phosphine ligand are applied to a catalyst composition used for hydroformylation of olefin, N/I (ratio of normal to iso) selectivity is reduced, and catalytic activity and stability are improved, as compared to a conventional catalyst composition to which either a phosphite ligand or a phosphine ligand is applied. The present invention has been completed based on this finding.

The catalyst composition according to the present invention contains: a monodentate phosphite ligand; a monodentate phosphine ligand; and a transition metal catalyst.

The respective ingredients of the catalyst composition will be described below in detail.

For example, the monodentate phosphite ligand may be a compound represented by the following Formula 1.

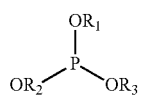

Formula 1 wherein $R_1$, $R_2$ and $R_3$ are each independently, for example, a substituted or unsubstituted alkyl group having 1 to 20 carbon atoms; a substituted or unsubstituted cycloalkyl or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted heterocyclic group having 4 to 36 carbon atoms, wherein the heteroalkyl group, the heteroaryl group and the heterocyclic group for example contain one or more atoms selected from the group consisting of N, O and S, and when $R_1$, $R_2$ and $R_3$ are substituted by a substituent, the substituent is for example nitro (—$NO_2$), fluorine (—F), chlorine (—Cl), bromine (—Br) or an alkyl group having 1 to 20 carbon atoms.

Specifically, examples of the monodentate phosphite ligand include one or more selected from the group consisting of triphenyl phosphite, tris(2,6-triisopropyl)phosphite, tris(2,6-di-tert-butyl-4-methoxyphenyl)phosphite, tris(2-tert-butyl-4-methylphenyl)phosphite and tris(2,4-di-tert-butylphenyl)phosphite (TDTBPP). In this case, there is an effect in that an N/I ratio (ratio of normal to iso) of aldehyde can be reduced.

The monodentate phosphine ligand may be for example a compound represented by the following Formula 2.

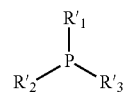

Formula 2 wherein $R'_1$, $R'_2$ and $R'_3$ are each independently, for example, a substituted or unsubstituted alkyl group having 1 to 20 carbon atoms; a substituted or unsubstituted cycloalkyl or cycloalkenyl group having 5 to 20 carbon atoms; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted heterocyclic group having 4 to 36 carbon atoms, wherein the heteroalkyl group, the heteroaryl group and the heterocyclic group for example contain one or more atoms selected from the group consisting of N, O and S, and when $R'_1$, $R'_2$ and $R'_3$ are substituted by a substituent, the substituent is for example nitro (—$NO_2$), fluorine (—F), chlorine (—Cl), bromine (—Br) or an alkyl group having 1 to 20 carbon atoms.

Specifically, examples of the monodentate phosphine ligand include one or more selected from the group consisting of tri-m-tolylphosphine (TMTP), tri-p-tolylphosphine (TPTP), diphenyl(p-tolyl)phosphine (DPPTP), cyclohexyldiphenylphosphine (CHDP), tris(2,6-dimethoxyphenyl)phosphine (TDMPP), tris(4-methoxyphenyl)phosphine (TMPP), trimesitylphosphine (TMSTP), tris-3,5-xylylphosphine (TXP), tricyclohexylphosphine (TCHP), tribenzylphosphine (TBP), benzyl diphenylphosphine (BDPP) and diphenyl-n-propylphosphine (DPMPP). In this case, there are effects of superior catalytic activity and stability.

The monodentate phosphite ligand and the monodentate phosphine ligand may each be present in an amount of 0.5 to 32.5 moles, 1 to 30 moles, 1 to 25 moles, or 5 to 20 moles, based on 1 mole of the transition metal catalyst. In this case, there are effects of superior catalytic activity and reaction rate.

The entire ligand including the monodentate phosphite ligand and the monodentate phosphine ligand may, for example, be present in an amount of 1 to 33 moles, 1 to 30 moles, 1 to 29 moles, 10 to 29 moles, or 15 to 29 moles, based on 1 mole of the transition metal catalyst. In this case, there is an effect of superior catalyst stability.

A mix ratio between the monodentate phosphite ligand and the monodentate phosphine ligand may, for example, be 5:1 to 1:5, 3:1 to 1:3, or 2:1 to 1:2, based on weight. In this case, there is an effect of reducing an N/I ratio (ratio of normal to iso) of aldehyde.

The transition metal catalyst may, for example, be a catalyst represented by the following Formula 3.

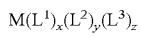

Formula 3 wherein M may, for example, be selected from the group consisting of cobalt (Co), rhodium (Rh), iridium (Ir), ruthenium (Ru), iron (Fe), nickel (Ni), palladium (Pd), platinum (Pt) and osmium (Os), $L^1$, $L^2$ and $L^3$ may, for example, be each independently selected from the group consisting of hydrogen, carbonyl (CO), cyclooctadiene, norbornene, chlorine, triphenylphosphine (TPP) and acetylacetonato (AcAc), and x, y and z may, for example, be each independently 0 to 5, with the proviso that all of x, y and z are not zero.

Specifically, examples of the transition metal catalyst include one or more selected from the group consisting of cobalt carbonyl [$Co_2(CO)_8$], acetylacetonato dicarbonyl rhodium [Rh(AcAc) $(CO)_2$], acetylacetonato carbonyl triphenylphosphine rhodium [Rh(AcAc)(CO) (TPP)], hydridocarbonyltri(triphenylphosphine) rhodium [HRh(CO) $(TPP)_3$], acetylacetonatodicarbonyl iridium [Ir(AcAc) $(CO)_2$] and hydridocarbonyltri(triphenylphosphine) iridium [HIr(CO)$(TPP)_3$]. In this case, there is an effect of superior catalytic activity.

The transition metal catalyst may, for example, be present in an amount of 1 to 1,000 ppm, 10 to 800 ppm, or 50 to 500 ppm, based on the catalyst composition. Within this range, there is an effect of superior hydroformylation rate.

The catalyst composition may, for example, contain further one or more solvents selected from the group consisting of propane aldehyde, butyl aldehyde, pentyl aldehyde, valeraldehyde, acetone, methyl ethyl ketone, methyl isobutyl ketone, acetophenone, cyclohexanone, ethanol, pentanol, octanol, hexanol, benzene, toluene, xylene, orthodichlorobenzene, tetrahydrofuran, dimethoxyethane, dioxane, methylene chloride and heptane. In this case, there is an effect of superior catalyst stability.

The hydroformylation method according to the present invention includes reacting an olefin-based compound with a synthetic gas ($CO/H_2$) of carbon monoxide and hydrogen in the presence of the catalyst composition to prepare aldehyde.

The olefin-based compound may, for example, be a compound represented by the following Formula 4.

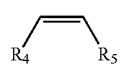

Formula 4 wherein $R_4$ and $R_5$ are, for example, each independently hydrogen, an alkyl group having 1 to 20 carbon atoms, fluorine (F), chlorine (Cl), bromine (Br), trifluoromethyl (—$CF_3$) or an aryl group having 6 to 20 carbon atoms and having 0 to 5 substituents, wherein the substituent of the aryl group is for example nitro (—$NO_2$), fluorine (—F), chlorine (—Cl), bromine (—Br), methyl, ethyl, propyl or butyl.

Specifically, the olefin-based compound may include one or more selected from the group consisting of ethene, propene, 1-butene, 1-pentene, 1-hexene, 1-octene and styrene.

A mix ratio of carbon monoxide to hydrogen of the synthetic gas ($CO/H_2$) may be 5:95 to 70:30, 40:60 to 60:40, or 45:55 to 55:45, on a mole basis. Within this range, there is an effect in that catalyst reactivity is superior because the gas used for reaction does not accumulate in the reactor.

There is no particular limitation as to the hydroformylation method of the olefin-based compound according to the present invention so long as a catalyst composition is used for the hydroformylation method.

For example, concerning the hydroformylation method, a temperature at which the olefin-based compound reacts with the synthetic gas ($CO/H_2$) in the presence of a catalyst composition may be 20 to 180° C., 50 to 150° C., or 75 to 125° C. In this case, there is an effect of maintaining catalyst stability and activity during hydroformylation.

In another example, concerning the hydroformylation method, a reaction pressure in the reactor may be 1 to 700 bar, 1 to 300 bar, or 5 to 30 bar. Within this range, there is an effect of superior catalytic activity.

The hydroformylation method of the olefin-based compound may, for example, be represented by the following Reaction Scheme 1.

[Reaction Scheme 1]

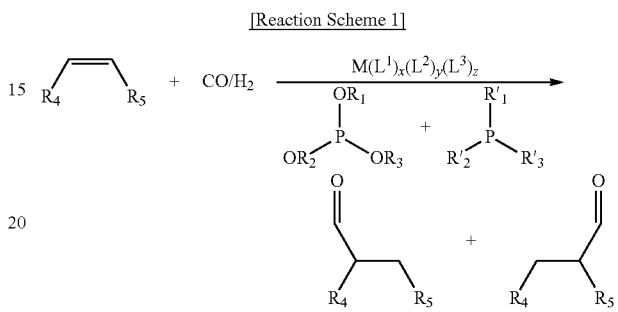

Specifically, for example, aldehyde can be prepared by dissolving the transition metal catalyst represented by Formula 3, and the monodentate phosphite ligand and the monodentate phosphine ligand represented by Formulae 1 and 2 in the solvent to prepare a mixed solution of a transition metal catalyst and a ligand, charging the mixed solution, the olefin-based compound represented by Formula 4 and the synthetic gas ($CO/H_2$) in an ordinary reactor and performing hydroformylation at an elevated temperature and a predetermined pressure while stirring.

The normal/iso ratio of aldehyde prepared by hydroformylation method of the olefin-based compound may, for example, be 1.5 to 3.0, 1.8 to 2.95, or 1.95 to 2.95.

Although preferred examples of the present invention will be provided for better understanding of the present invention, these examples are provided only for illustration of the present invention. Those skilled in the art will appreciate that various modifications, additions and substitutions are possible, without departing from the scope and spirit of the invention as disclosed in the accompanying claims. Obviously, such modifications, additions and substitutions fall under the scope of the claims.

EXAMPLE

Reference Example 0.12 g (0.3 mmol) of rhodium acetylacetonato carbonyl triphenylphosphine (Rh(AcAc) (CO) (TPP), ROPAC) as a catalyst and triphenylphosphine (TPP) were dissolved in a valeraldehyde solvent according to molar ratios as set forth in Table 1 given below such that the entire solution reached 100 g (Rh 250 ppm, TTP 6 wt %) and the resulting solution was then charged into a 600 ml autoclave reactor. The reaction solution was reacted with propylene and a synthetic gas ($CO/H_2$) for one hour while maintaining an inner pressure of the reactor at 8 bar and stirring at 90° C.

Examples 1 to 4

Catalyst compositions were prepared in the same manner as in Reference Example except that a phosphite compound (L1) and a phosphine compound (L2) were added as ligands in moles as set forth in Table 1, instead of triphenylphosphine (TPP).

Comparative Examples 1 to 4

Catalyst compositions were prepared in the same manner as in Reference Example except that a phosphite compound (L1) was added in a mole as set forth in Table 1 as a ligand, instead of triphenylphosphine (TPP).

Comparative Examples 5 to 10

Catalyst compositions were prepared in the same manner as in Reference Example except that a phosphine compound (L2) was added in a mole as set forth in Table 1 as a ligand, instead of triphenylphosphine (TPP).

Comparative Examples 11 to 14

Catalyst compositions were prepared in the same manner as in Reference Example except that a phosphite compound (L1) and a phosphine compound (L2) were added in moles as set forth in Table 1 as ligands, instead of triphenylphosphine (TPP).

Comparative Examples 15 and 16

Catalyst compositions were prepared in the same manner as in Reference Example except that a bidentate phosphite compound (L3) and a phosphine compound (L2) were added in moles as set forth in Table 2 as ligands, instead of triphenylphosphine (TPP).

Comparative Examples 17 and 18

Catalyst compositions were prepared in the same manner as in Reference Example except that a phosphite compound (L1) and a phosphite compound (L1') were added in moles as set forth in Table 3 as ligands, instead of triphenylphosphine (TPP).

Comparative Examples 19 and 20

Catalyst compositions were prepared in the same manner as in Reference Example except that a phosphine compound (L2) and a phosphine compound (L2') were added as set forth in Table 4 as ligands, instead of triphenylphosphine (TPP).

Test Example

The catalytic activity, catalyst stability and n/i ratios of aldehyde of catalyst compositions prepared in Reference Example, Examples 1 to 4 and Comparative Examples 1 to 20 were measured in accordance with the following methods and are shown in Table 1.

Measurement Method

Catalytic activity (normal activity, %): the total amount of normal and isobutyl aldehydes produced by reaction in accordance with each of Examples and Comparative Examples, was compared with respect to the total amount of normal and isobutyl aldehydes produced by reaction in accordance with Comparative Example, based on 100%, and catalytic activity was calculated and expressed as a percentage in accordance with the following Equation 1.

Catalytic activity=the total amount of normal and isobutyl aldehydes of Example or Comparative Example/the total amount of normal and isobutyl aldehydes of Reference Example×100 [Equation 1]

Catalyst stability (normal stability, %): obtained by performing reaction in accordance with Reference Example, measuring the amount of propylene gas used for reaction, inactivating catalyst solutions prepared in Examples and Comparative Examples for 24 hours, conducting hydroformylation in the same manner as above, measuring the amount of propylene gas used for reaction, comparing the amount of consumed propylene gas before inactivation of Reference Example with the amount of consumed propylene gas after inactivation of Example or Comparative Example for 24 hours, calculating catalyst stability in accordance with the following Equation 2 and expressing the same as a percentage.

Catalyst stability=amount of propylene gas consumed during reaction after inactivation of Example or Comparative Example for 24 hours/amount of consumed propylene gas before inactivation of Reference Example×100 [Equation 2]

Normal/iso selectivity (n/i ratio) of aldehyde: the value was obtained by dividing the amount of produced normal-butyraldehyde by the amount of iso-butyraldehyde and the amounts of produced aldehydes were obtained by gas chromatography (GC) analysis after reaction.

TABLE 1

| Item | Catalyst (Rh) | L1 | L2 | L1/Rh (mol/mol) | L2/Rh (mol/mol) | n/i ratio | Activity (%) | Stability (%) |
|---|---|---|---|---|---|---|---|---|
| Ref. Ex. | ROPAC | — | TPP | — | 94 | 10 | 100 | 100 |
| Ex. 1 | ROPAC | TDTBPP | CHDP | 12.7 | 15.3 | 2.01 | 108 | 210 |
| Ex. 2 | ROPAC | TDTBPP | CHDP | 6.3 | 15.3 | 2.03 | 121 | 84 |
| Ex. 3 | ROPAC | TDTBPP | TPTP | 12.7 | 13.5 | 2.42 | 224 | 130 |
| Ex. 4 | ROPAC | TDTBPP | TPTP | 6.3 | 13.5 | 2.92 | 250 | 77 |
| Comp. Ex. 1 | ROPAC | TDTBPP | — | 6.3 | — | 1.05 | 289 | 5 |
| Comp. Ex. 2 | ROPAC | TDTBPP | — | 12.7 | — | 1.06 | 335 | 5 |
| Comp. Ex. 3 | ROPAC | TDTBPP | — | 19 | — | 1.09 | 428 | 7 |
| Comp. Ex. 4 | ROPAC | TDTBPP | — | 25.4 | — | 1.11 | 397 | 7 |
| Comp. Ex. 5 | ROPAC | — | CHDP | — | 15.3 | 1.96 | 67 | 61 |
| Comp. Ex. 6 | ROPAC | — | CHDP | — | 30.6 | 2.07 | 43 | 88 |
| Comp. Ex. 7 | ROPAC | — | CHDP | — | 45.9 | 2.18 | 34 | 121 |
| Comp. Ex. 8 | ROPAC | — | TPTP | — | 13.5 | 2.9 | 112 | 41 |
| Comp. Ex. 9 | ROPAC | — | TPTP | — | 27 | 3.6 | 105 | 62 |
| Comp. Ex. 10 | ROPAC | — | TPTP | — | 40.5 | 4.2 | 103 | 91 |
| Comp. Ex. 11 | ROPAC | TDTBPP | CHDP | 6.3 | 30.6 | 2.13 | 43 | 120 |
| Comp. Ex. 12 | ROPAC | TDTBPP | CHDP | 12.7 | 30.6 | 2.61 | 37 | 230 |
| Comp. Ex. 13 | ROPAC | TDTBPP | TPTP | 6.3 | 27 | 3.34 | 94 | 101 |
| Comp. Ex. 14 | ROPAC | TDTBPP | TPTP | 12.7 | 27 | 3.23 | 87 | 187 |

*TDTBPP: Tris (2,4-di-tert-butylphenyl) phosphite
*CHDP: Cyclohexyldiphenylphosphine
*TPTP: Tri-p-tolylphosphine As can be seen from Table 1, catalyst compositions of Examples 1 to 4 prepared according to the present invention maintained similar or superior catalytic activity and stability, and significantly reduced normal/iso selectivity (n/i ratio) of produced aldehyde, as compared to Reference Example.

However, Comparative Examples 1 to 4 in which only a phosphite compound was used as a ligand exhibited significant deterioration in catalyst stability and Comparative Examples 5 to 10 in which only a phosphine compound was used as a ligand exhibited deteriorated catalytic activity or did not exhibit a level of selectivity desired in the present invention.

In addition, when the contents of phosphite ligand and phosphine ligand are not within predetermined ranges, catalytic activity was deteriorated or selectivity could not reach a desired level, as can be seen from Comparative Examples 11 to 14.

TABLE 2

| Item | Catalyst (Rh) | L2 | L3 | L2/Rh (mol/mol) | L3/Rh (mol/mol) | n/i ratio | Activity (%) | Stability (%) |
|---|---|---|---|---|---|---|---|---|
| Comp. Ex. 15 | ROPAC | CHDP | PCA-4 | 30.6 | 5.13 | 18.1 | 80 | 110 |
| Comp. Ex. 16 | ROPAC | CHDP | PCA-4 | 15.3 | 10.3 | 26.2 | 17 | 5 |

*PCA-4 (bidentate phosphite):
1,2-bis((4,8-di-tert-butyl-2,10-dimethyl-12H-dibenzo[d,g][1,3,2]dioxaphosphocin-6-yl)oxy)ethane As can be seen from Table 2, Comparative Examples 15 and 16 in which both bidentate phosphite, rather than monodentate phosphite, and monodentate phosphine were used as ligands exhibited a significant increase in normal/iso selectivity (n/i ratio) of produced aldehyde.

TABLE 3

| Item | Catalyst (Rh) | L1 | L1' | L1/Rh (mol/mol) | L1'/Rh (mol/mol) | n/i ratio | Activity (%) | Stability (%) |
|---|---|---|---|---|---|---|---|---|
| Comp. Ex. 17 | ROPAC | TDTBPP | TPPT | 12.7 | 13.2 | 4.13 | 180 | 12 |
| Comp. Ex. 18 | ROPAC | TDTBPP | TPPT | 6.3 | 26.4 | 5.37 | 225 | 10 |

*TPPT: Triphenyl phosphite

As can be seen from Table 3, Comparative Examples 17 and 18 in which two kinds of monodentate phosphites, rather than monodentate phosphite and monodentate phosphine, were used as ligands did not exhibit a level of normal/iso selectivity (n/i ratio) of produced aldehyde desired in the present invention and exhibited significant deterioration in catalyst stability.

TABLE 4

| Item | Catalyst (Rh) | L2 | L2' | L2/Rh (mol/mol) | L2'/Rh (mol/mol) | n/i ratio | Activity (%) | Stability (%) |
|---|---|---|---|---|---|---|---|---|
| Comp. Ex.19 | ROPAC | CHDP | TMTP | 15.3 | 15.3 | 4.73 | 82 | 153 |
| Comp. Ex.20 | ROPAC | CHDP | TMTP | 15.3 | 30.6 | 4.27 | 79 | 97 |

*TMTP: tri-m-tolylphosphine

As can be seen from Table 4, Comparative Examples 19 and 20 in which two kinds of monodentate phosphines, rather than monodentate phosphite and monodentate phosphine, were used as ligands did not exhibit a level of normal/iso selectivity (n/i ratio) of produced aldehyde desired in the present invention and exhibited significant deterioration in catalyst stability.

From the foregoing, a case in which both a monodentate phosphite ligand and a monodentate phosphine ligand are applied to a transition metal catalyst according to the present invention is preferred in terms of cost and commercial applicability because expensive ligands can be used in appropriate amounts. It can be seen from this that catalytic activity and stability can be maintained and N/I (ratio of normal to iso) selectivity of aldehyde produced by hydroformylation of an olefin-based compound can be considerably reduced using the catalyst composition.

What is claimed is:

1. A catalyst composition comprising:
   a monodentate phosphite ligand represented by the following Formula 1;
   a monodentate phosphine ligand represented by the following Formula 2; and
   a transition metal catalyst represented by the following Formula 3,
   wherein the total content of the entire ligand including the monodentate phosphite ligand and the monodentate phosphine ligand is 1 to 33 moles, based on 1 mole of the transition metal catalyst,

[Formula 1]

[Formula 2]

wherein $R_1$, $R_2$, $R_3$, $R'_1$, $R'_2$ and $R'_3$ each independently represent: a substituted or unsubstituted alkyl group having 1 to 20 carbon atoms; a substituted or unsubstituted cycloalkyl or cycloalkenyl group having 5 to 20 carbon atoms group; a substituted or unsubstituted aryl group having 6 to 36 carbon atoms; a substituted or unsubstituted heteroalkyl group having 1 to 20 carbon atoms; a substituted or unsubstituted heteroaryl group having 4 to 36 carbon atoms; or a substituted or unsubstituted heterocyclic group having 4 to 36 carbon atoms,
wherein the heteroalkyl group, the heteroaryl group and the heterocyclic group contain one or more atoms selected from the group consisting of N, O and S, and when $R_1$, $R_2$, $R_3$, $R'_1$, $R'_2$ and $R'_3$ are substituted by a substituent, the substituent is nitro (—$NO_2$), fluorine (—F), chlorine (—Cl), bromine (—Br) or an alkyl group having 1 to 20 carbon atoms,

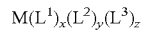

[Formula 3]

wherein M is one selected from the group consisting of cobalt (Co), rhodium (Rh), iridium (Ir), ruthenium (Ru), iron (Fe), nickel (Ni), palladium (Pd), platinum (Pt) and osmium (Os), $L^1$, $L^2$ and $L^3$ each independently represent one selected from the group consisting of hydrogen, carbonyl (CO), cyclooctadiene, norbornene, chlorine, triphenylphosphine (TPP) and acetylacetonato (AcAc), and x, y and z each independently represent 0 to 5, with the proviso that all of x, y and z are not zero.

2. The catalyst composition according to claim 1, wherein the content of each of the monodentate phosphite ligand and the monodentate phosphine ligand is 0.5 to 32.5 moles, based on 1 mole of the transition metal catalyst.

3. The catalyst composition according to claim 1, wherein a mix ratio of the monodentate phosphite ligand and the monodentate phosphine ligand is 5:1 to 1:5, based on weight.

4. The catalyst composition according to claim 1, wherein the monodentate phosphite ligand comprises one or more selected from the group consisting of triphenyl phosphite, tris(2,6-triisopropyl)phosphite, tris(2,6-di-tert-butyl-4-methoxyphenyl)phosphite, tris(2-tert-butyl-4-methylphenyl)phosphite and tris(2,4-di-tert-butylphenyl)phosphite (TDTBPP).

5. The catalyst composition according to claim 1, wherein the monodentate phosphine ligand comprises one or more selected from the group consisting of tri-m-tolylphosphine (TMTP), tri-p-tolylphosphine (TPTP), diphenyl(p-tolyl)phosphine (DPPTP), cyclohexyldiphenylphosphine (CHDP), tris(2,6-dimethoxyphenyl)phosphine (TDMPP), tris(4-methoxyphenyl)phosphine (TMPP), trimesitylphosphine (TMSTP), tris-3,5-xylylphosphine (TXP), tricyclohexylphosphine (TCHP), tribenzylphosphine (TBP), benzyldiphenylphosphine (BDPP) and diphenyl-n-propylphosphine (DPMPP).

6. The catalyst composition according to claim 1, wherein the transition metal catalyst comprises one or more selected from the group consisting of cobalt carbonyl [$Co_2(CO)_8$], acetylacetonatodicarbonyl rhodium [$Rh(AcAc)(CO)_2$], acetylacetonatocarbonyltriphenylphosphine rhodium [Rh(AcAc)(CO)(TPP)], hydridocarbonyltri(triphenylphosphine)rhodium [$HRh(CO)(TPP)_3$], acetylacetonatodicarbonyl iridium [$Ir(AcAc)(CO)_2$] and hydridocarbonyltri(triphenylphosphine)iridium [$HIr(CO)(TPP)_3$].

7. The catalyst composition according to claim 1, further comprising one or more solvents selected from the group consisting of propane aldehyde, butyl aldehyde, pentyl aldehyde, valeraldehyde, acetone, methyl ethyl ketone, methyl isobutyl ketone, acetophenone, cyclohexanone, ethanol, pentanol, octanol, hexanol, benzene, toluene, xylene, orthodichlorobenzene, tetrahydrofuran, dimethoxyethane, dioxane, methylene chloride and heptane.

8. The catalyst composition according to claim 1, wherein the content of the transition metal catalyst is 1 to 1,000 ppm, based on the catalyst composition.

9. A hydroformylation method of an olefin-based compound comprising reacting an olefin-based compound with a synthetic gas ($CO/H_2$) of carbon monoxide and hydrogen in the presence of the catalyst composition according to claim 1, to prepare aldehyde.

10. The hydroformylation method according to claim 9, wherein the olefin-based compound is a compound represented by the following Formula 4:

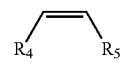

[Formula 4]

wherein $R_4$ and $R_5$ each independently represent hydrogen, an alkyl group having 1 to 20 carbon atoms, fluorine (F), chlorine (Cl), bromine (Br), trifluoromethyl ($-CF_3$) or an aryl group having 6 to 20 carbon atoms and having 0 to 5 substituents, wherein the substituent of the aryl group is nitro ($-NO_2$), fluorine (—F), chlorine (—Cl), bromine (—Br), methyl, ethyl, propyl or butyl.

11. The hydroformylation method according to claim 9, wherein the olefin-based compound comprises one or more selected from the group consisting of ethene, propene, 1-butene, 1-pentene, 1-hexene, 1-octene and styrene.

12. The hydroformylation method according to claim 9, wherein a normal/iso ratio of the produced aldehyde is 1.5 to 3.0.

13. The hydroformylation method according to claim 9, wherein a mix ratio of carbon monoxide and hydrogen in the synthetic gas ($CO/H_2$) is 5:95 to 70:30, on a mole basis.

* * * * *